US009636445B2

(12) United States Patent
Jonsson et al.

(10) Patent No.: US 9,636,445 B2
(45) Date of Patent: May 2, 2017

(54) AMBULATORY ULTRAFILTRATION DEVICE WITH CONTROL UNIT PROGRAMMED TO CONTROL A DRIVE FLUID PUMP TO PERFORM ULTRAFILTRATION

(75) Inventors: Lennart Jonsson, Bjarred (SE); Jan Sternby, Lund (SE); Anders Wieslander, Lund (SE)

(73) Assignee: Gambro Lundia AB, Lund (SE)

( * ) Notice: Subject to any disclaimer, the term of this patent is extended or adjusted under 35 U.S.C. 154(b) by 800 days.

(21) Appl. No.: 13/808,770

(22) PCT Filed: Jun. 16, 2011

(86) PCT No.: PCT/EP2011/060019
§ 371 (c)(1),
(2), (4) Date: May 10, 2013

(87) PCT Pub. No.: WO2012/004103
PCT Pub. Date: Jan. 12, 2012

(65) Prior Publication Data
US 2013/0228516 A1    Sep. 5, 2013

Related U.S. Application Data

(60) Provisional application No. 61/361,454, filed on Jul. 5, 2010.

(30) Foreign Application Priority Data

Jul. 5, 2010    (SE) ..................................... 1050739

(51) Int. Cl.
*B01D 11/00*    (2006.01)
*B01D 61/00*    (2006.01)
(Continued)

(52) U.S. Cl.
CPC .............. *A61M 1/30* (2013.01); *A61M 1/302* (2014.02); *A61M 1/303* (2014.02);
(Continued)

(58) Field of Classification Search
CPC ...... A61M 1/16; A61M 1/165; A61M 1/1656; A61M 1/30; A61M 1/302; A61M 1/303;
(Continued)

(56) References Cited

U.S. PATENT DOCUMENTS 4,269,708 A    5/1981    Bonomini et al.
4,552,552 A *  11/1985   Polaschegg ......... A61M 1/1037
                                            210/416.1
(Continued)

FOREIGN PATENT DOCUMENTS

CN    101505811    5/2012
DE    41 14 908 A1    11/1992
(Continued)

OTHER PUBLICATIONS

Clark, W.R., "Extracorporeal ultrafiltration for acute exacerbations of chronic heart failure: Report from the Acute Dialysis Quality Initiative," The International Journal of Artificial Organs, vol. 28, No. 5, 2005, pp.
(Continued)

*Primary Examiner* — Dirk Bass
*Assistant Examiner* — Hayden Brewster
(74) *Attorney, Agent, or Firm* — K&L Gates LLP

(57) ABSTRACT

An ambulatory ultrafiltration device includes a blood filter that has a blood side or fluid communication with the vascular system of the subject, an ultrafiltrate side, and a semipermeable membrane disposed between the blood side and the ultrafiltrate side. The ambulatory ultrafiltration also includes a buffer vessel in fluid communication with the blood side of the blood filter, and a blood pump. The blood
(Continued)

pump is controlled to alternate between a withdrawal phase and a return phase. In the withdrawal phase, blood is withdrawn on a blood path from the subject via the blood filter to the buffer vessel. In the return phase, blood is returned from the buffer vessel to the subject on the blood path. The blood filter is arranged to remove ultrafiltrate from the blood during at least one of the withdrawal and return phases.

29 Claims, 7 Drawing Sheets

(51) Int. Cl.
*A61M 1/30* (2006.01)
*A61M 1/34* (2006.01)
*C02F 9/00* (2006.01)
*A61M 1/36* (2006.01)

(52) U.S. Cl.
CPC ........ *A61M 1/3427* (2014.02); *A61M 1/3604* (2014.02); *A61M 1/365* (2014.02); *A61M 1/3672* (2013.01); *A61M 2209/088* (2013.01)

(58) Field of Classification Search
CPC .. A61M 1/3427; A61M 1/365; A61M 1/3604; A61M 1/3643; A61M 1/3672; A61M 2001/3437; A61M 2209/088; B01D 11/00; B01D 13/01; B01D 21/30
USPC ... 210/136, 195.1, 195.2, 257.1, 257.2, 258, 210/321.71–321.89, 416.1, 646, 647; 422/44–48
See application file for complete search history.

(56) References Cited

U.S. PATENT DOCUMENTS

| | | | |
|---|---|---|---|
| 4,897,189 A * | 1/1990 | Greenwood et al. | 210/195.2 |
| 6,645,166 B2 * | 11/2003 | Scheunert | A61M 1/30 210/645 |
| 7,311,689 B2 | 12/2007 | Levin et al. | |
| 8,241,239 B2 | 8/2012 | Solomon et al. | |
| 2001/0032818 A1 | 10/2001 | Nikaido et al. | |
| 2003/0097087 A1 * | 5/2003 | Gura | 604/6.09 |
| 2005/0126962 A1 | 6/2005 | Nilsson | |
| 2011/0046535 A1 * | 2/2011 | Jonsson | A61M 1/106 604/6.11 |

FOREIGN PATENT DOCUMENTS

| | | |
|---|---|---|
| EP | 0 105 845 A1 | 4/1984 |
| EP | 1 509 232 B1 | 3/2005 |
| EP | 2 140 889 A1 | 1/2010 |
| WO | 2004/026364 A2 | 4/2004 |
| WO | 2009100154 | 8/2009 |
| WO | 2009157877 | 12/2009 |
| WO | 2010062716 | 6/2010 |
| WO | 2012127298 | 9/2012 |

OTHER PUBLICATIONS

Nissenson et al., Handbook of Dialysis Therapy, Chapter 25 Isolated Ultrafiltration John J. White, MD, et al., 4th Edition ISBN: 978-1-4160-4197-9, Title Page, pp. 393-404.

* cited by examiner

AMBULATORY ULTRAFILTRATION DEVICE WITH CONTROL UNIT PROGRAMMED TO CONTROL A DRIVE FLUID PUMP TO PERFORM ULTRAFILTRATION

TECHNICAL FIELD

The present invention relates to removal of excessive fluids, such as blood water, in a human or animal subject. In particular, the present invention relates to a technique for providing an ambulatory ultrafiltration device for connection to the vascular system of the subject.

BACKGROUND

Ultrafiltration (UF) encompasses a variety of membrane filtration techniques in which hydrostatic pressure forces a liquid against a semipermeable membrane.

In blood treatment, UF generally denotes a process of removing water from blood plasma. Blood is passed on a blood side of a blood filter, and a gradient of pressure is created through the semipermeable membrane. The pressure gradient forces fluid through the pores of the membrane. The pores filter electrolytes and small and middle sized molecules (up to 20,000 to 30,000 daltons) from the blood plasma. In contrast to the plasma, the ultrafiltrate output from the filtration pores lacks the plasma proteins and cellular components of plasma. Since the concentration of small solutes is the same in the ultrafiltrate as in the plasma, fluid volume is removed without any change in the plasma concentration.

Slow Continuous Ultrafiltration (SCUF) is a continuous therapy which is designed to approximately mimic the ultrafiltration function of the kidneys. During SCUF, blood is removed from the body of a subject and passed in an extracorporeal circuit through a blood filter, where a predetermined percentage of plasma water is removed based upon a prescription. Typically, no more than 2 liters an hour of fluid is removed. The remaining blood is returned to the patient. Unlike hemodialysis, hemofiltration and hemodiafiltration, no dialysis fluid or replacement fluids are used in SCUF.

SCUF may, e.g., be employed for treatment of congestive heart failure (CFH) or other conditions leading to fluid overload in a subject. CHF is a condition that occurs when the heart becomes damaged and reduces blood flow to the organs of the body. If blood flow decreases to a certain degree, kidney function becomes impaired and results in fluid retention, abnormal hormone secretions and increased constriction of blood vessels. This results in increased workload of the heart and further decrease of the heart's pumping ability which, in turn, causes further reductions in blood flow to the kidney. It is believed that the progressively-decreasing perfusion of the kidney is the principal non-cardiac cause perpetuating the downward spiral of the so-called "Vicious Cycle" of CHF. Moreover, the fluid overload and associated clinical symptoms resulting from these physiologic changes may be seen as the predominant cause for excessive hospital admissions, terrible quality of life and overwhelming costs to the health care system due to CHF. This fluid overload can be removed by means of SCUF.

SCUF may also be used as a supplementary treatment to dialysis, such as hemodialysis. Hemodialysis is a standard technique for treating patients suffering from acute or chronic renal failure. Hemodialysis treatments are traditionally carried out about three times a week, whereby the blood is purified and the liquid balance of the patient is adjusted at a hemodialysis site in a clinic. Since the kidneys of a patient suffering for renal conditions usually do not produce any significant amounts of urine, the patient may turn up at the hemodialysis site with an excess of liquid in the body. After the hemodialysis treatment, the patient may instead have a shortage of liquid in the body. By subjecting the patient to SCUF in between the ordinary hemodialysis treatments, it is possible to equalize the liquid level over time and thereby reduce the strain on the patient's body caused by fluctuating liquid levels.

SCUF may also be used for treatment of anuric patients treated by peritoneal dialysis (PD), which may experience fluid overload.

It is generally desirable that the subjects/patients are able to perform a SCUF treatment outside of a clinical environment, e.g. at home. Specifically, there is a need for an ambulatory ultrafiltration device that enables continual, steady and smooth removal of excess fluid from the body of a subject, preferably while being worn by the subject.

WO2004/026364 discloses an ultrafiltration device adapted to be worn on a portion of a body of a patient. The device includes a blood filter including a blood inlet tube leading from a first blood vessel and blood outlet tube leading to a second blood vessel in the patient. A blood pump forces the patient's blood through the filter. Excess fluid is separated by the blood filter and drained into an excess fluid bag.

A similar device is disclosed in EP1509262, which includes a blood filter with an inlet for connection to an artery of a patient and an outlet for connection to a vein of the patient. Blood is driven to continuously flow through the extracorporeal circuit by the inherent pressure difference between the artery and the vein, and the excess fluid which is separated by the blood filter is drained into a filtrate container.

These wearable devices thus require connection of two access devices (needle catheters, etc) to the vascular system of the patient. This also means that there is a risk for severe blood loss if the venous access device is detached, since blood will be driven from the arterial access device through the blood filter and out of the detached venous access device. The risk for detachment of an access device may be elevated in a wearable device, and the resulting blood loss may be significant, especially if the device operates continuously, albeit at a low blood flow rate. The need for access to two blood vessels may also be undesirable, in particular if the device is to be installed by persons without medical training and experience, e.g. by the subject itself.

U.S. Pat. No. 7,311,689 discloses an ultrafiltration device which is not portable, let alone wearable, but which is designed to perform SCUF for removal of excessive liquid in patients suffering from CHF. In one disclosed embodiment, the device is connected to the vascular system of the patient by means of a single needle. The device comprises a bifurcated line set with a first branch for connecting the needle to a bag via a pump, and a second branch for connecting the needle to the bag via a blood filter and the pump. A valve is arranged in each of the first and second branches. The device operates in a withdrawal phase, in which the pump and the valves are operated such that blood is withdrawn via the needle into the first branch, thereby bypassing the filter, and stored in the bag. Then, in a return phase, the pump and the valves are operated such that blood is ejected from the bag into the second branch for transport back to the patient. In the return phase, ultrafiltration occurs as the blood passes the blood filter, and the resulting ultrafiltrate is collected in a bag connected to the filter. Apart from not being designed for ambulatory treatment, this device has an elevated risk for clotting and/or coagulation of the blood in the bifurcated line set, since blood is stagnant in one branch while blood is transported in the other. Furthermore, compared to the above-identified wearable devices, more blood is contained in extracorporeal circuit and is exposed to a larger surface area of foreign material. Still further, the disclosed embodiment necessitates the use and control of valves, and the additional structural complexity may lead to an increased risk of system failure.

SUMMARY

It is an object of the invention to at least partly overcome one or more of the limitations of the prior art.

In view of the foregoing, one object is to provide an ultrafiltration device suitable for ambulatory blood treatment and with a low risk for uncontrolled bleeding.

It is another object to enable an ambulatory ultrafiltration device with a small and compact design.

A still further object is to provide an ambulatory ultrafiltration device which is simple to install and handle even for individuals without medical training.

Yet another object is to provide an ambulatory ultrafiltration device which is dependable in operation.

One or more of these objects, and further objects that may appear from the description below, are at least partly achieved by means of an ambulatory ultrafiltration device, a system for ultrafiltration of blood, a method for controlling an ambulatory ultrafiltration device, a computer readable medium and a method for ultrafiltration of blood according to the independent claims, embodiments thereof being defined by the dependent claims.

A first aspect of the invention is an ambulatory ultrafiltration device for connection to the vascular system of a subject. The ambulatory ultrafiltration device comprises: a blood filter having a blood side configured for fluid communication with the vascular system of the subject, an ultrafiltrate side, and a semipermeable membrane disposed between the blood side and the ultrafiltrate side; a buffer vessel in fluid communication with the blood side of the blood filter; and a blood pump operable to alternate between a withdrawal phase and a return phase, wherein the withdrawal phase comprises blood being withdrawn on a blood path from the subject via the blood filter to the buffer vessel, and the return phase comprises blood being returned from the reservoir to the subject on said blood path; wherein the blood filter is arranged to remove ultrafiltrate from the blood during at least one of the withdrawal and return phases.

The ultrafiltration device of the first aspect enables a simple and compact construction centered around a single blood path for withdrawal of blood from the subject and return of treated blood to the subject, thereby making the device suitable for ambulatory treatment. Furthermore, the ultrafiltration device enables the use of a single access device for establishing the blood path between the subject and the buffer vessel, which may be a desirable feature in a device for ambulatory treatment, since it minimizes the risk for uncontrolled bleeding if the access device is detached from the vascular system of the subject. Still further, since the blood is transported back and forth on a single blood path while being subjected to ultrafiltration, no blood will be left stagnant in the blood path except during the transition between the withdrawal and return phases. This will reduce the risk for clotting/coagulation of blood in the blood filter or in the blood lines that connect the blood filter to the subject and the reservoir, respectively. Furthermore, compared to the use of a bifurcated blood path, the use of a single blood path may serve to reduce the exposure of the blood to foreign material in the blood path.

The ultrafiltration device may be controlled to remove the ultrafiltrate during the return phase. Thereby, the more concentrated blood that results from the ultrafiltration will have a short path to be transported before being returned to the subject.

Alternatively or additionally, the ultrafiltration device may be controlled to remove the ultrafiltrate during the withdrawal phase. This will increase the amount of withdrawn, and thus treated, blood for a given volume of blood being drawn into the buffer vessel. Thus, the efficiency of the device can be increased, e.g. enabling the size of the ultrafiltration device to be reduced for a given ultrafiltration rate.

The ultrafiltration device may be provided without the access device for connection to the vascular system of the subject and/or without any receptacle for collecting the ultrafiltrate. Instead, the ultrafiltration device may be provided with a connector for attaching an access device or a line set with an access device and/or a connector for attaching an ultrafiltrate receptacle. Thereby, the ultrafiltration device may be re-used for several treatments, whereas the access device/ultrafiltrate receptacle may be a disposable part. In a variant, the ultrafiltration device is configured as a disposable unit that may be integrated with an access device and/or an ultrafiltrate receptacle.

The ultrafiltration device of the first aspect may, but need not, be used for SCUF, typically using blood withdrawal rates and blood return rates of about 5-60 ml/min, and an average ultrafiltration rate of about 1-5 ml/min.

In one embodiment, the ambulatory ultrafiltration device further comprises means for supplying an anticoagulant to the blood path. This will further reduce the risk for clotting/coagulation of the blood in the blood path and/or in the buffer vessel. Any type of anticoagulant may be used, including without limitation heparin and citrate.

In one embodiment, the means for supplying an anticoagulant is operable to supply the anticoagulant via the semipermeable membrane. This provides a convenient way of supplying the anticoagulant, which may be accomplished by reversing the pressure gradient through the membrane. The ultrafiltration device may be given a compact design, since the need to attach additional connectors/couplings to the blood path to supply the anticoagulant may be obviated. The anticoagulant may be supplied during the withdrawal phase, to ensure that the anticoagulant is provided to the entire blood path and to the buffer vessel.

Alternatively or additionally, the anticoagulant may be injected elsewhere into the blood path, e.g. close to the access device that connects the ultrafiltration device to the vascular system of the subject.

When the blood is repeatedly transported back and forth along a single blood path, there is a risk that a certain fraction of the blood is caught in the blood path between the blood pump and the access device. This portion of the blood path is also denoted "dead space" herein. Thus, the dead space may contain a fraction of blood that is not subjected to ultrafiltration and/or that is not returned to the subject. This potential problem may be solved by minimizing the extent of this portion of the blood path. However, the dead space problem may also be overcome by providing the ambulatory ultrafiltration device with means for intermittently supplying a displacement liquid to the blood path, e.g. during the return phase. The displacement liquid will thereby move all or part of the blood from the dead space into the subject, thereby ensuring that this blood is no longer caught within the blood path. The ratio between return phases with supply of displacement liquid and regular return phases may be, e.g., 1:20, 1:15, 1:10, 1:5 or 1:2. Alternatively or additionally, the displacement liquid may be supplied to the blood path intermediate the return phase and the withdrawal phase. It may also be possible to intermittently supply the displacement liquid during withdrawal phases.

In one embodiment, the means for intermittently supplying a displacement liquid is operable to supply the displacement liquid via the semipermeable membrane. This provides a convenient way of supplying the displacement liquid, which may accomplished by reversing the pressure gradient through the membrane. The ultrafiltration device may be given a compact design, since the need to attach additional connectors/couplings to the blood path to supply the displacement liquid may be obviated.

In the foregoing embodiments, the displacement liquid may comprise an anticoagulant. Thereby, the supply of the displacement liquid has the dual effect of purging (part of) the dead space and counteracting the blood's predisposition to coagulate, which may reduce the operational complexity and/or enable a more compact design of the ultrafiltration device.

In the foregoing embodiments, the displacement liquid may comprise the ultrafiltrate. Thus, a small amount of ultrafiltrate may intermittently be re-introduced into the blood path to at least partially purge the blood in the dead space. This may serve to reduce the operational complexity and/or enable a more compact design of the ultrafiltration device. It may also serve to reduce the weight and size of the ultrafiltration device since it may obviate the need for storing a separate displacement liquid.

In one embodiment, the ambulatory ultrafiltration device further comprises means for selectively supplying a priming liquid to the blood path. The priming liquid is typically supplied at start-up of the ultrafiltration device, i.e. before connecting it to the vascular system of the subject, for the purpose of purging the blood path of air, and possibly contaminants.

The means for selectively supplying a priming liquid may be operable to supply the priming liquid via the semipermeable membrane. This provides a convenient way of supplying the priming liquid, which may accomplished by reversing the pressure gradient through the membrane. The ultrafiltration device may be given a compact design, since the need to attach additional connectors/couplings to the blood path to supply the priming liquid may be obviated.

In one embodiment, the receptacle for ultrafiltrate, which is attached to or included in the ultrafiltration device, is pre-loaded with an amount of priming liquid, which is supplied to the blood path at start-up of the ultrafiltration device.

In one embodiment, the ambulatory ultrafiltration device further comprises a membrane chamber which defines a blood side and a drive fluid side separated by a flexible membrane or diaphragm, and a drive fluid pump in fluid communication with the drive fluid side, wherein the blood side of the membrane chamber is connected in fluid communication with the blood side of the blood filter so as to form the buffer vessel, and wherein the drive fluid pump is operable to pump a drive fluid out of and into the drive fluid side of the membrane chamber, so as to generate the withdrawal and return phases. Here, the membrane chamber functions both as buffer vessel and part of the blood pump. This enables a simplified and compact design. The drive fluid pump that drives the membrane (diaphragm) in the membrane chamber and the withdrawal phase and return phases is arranged to pump drive fluid, which typically is not blood. The requirements on a pump for pumping drive fluid are thus generally lower compared to a pump for pumping blood. This may serve to lower cost and complexity of the ultrafiltration device.

In one embodiment, the ultrafiltrate side of the blood filter is configured for connection to a receptacle for receiving the ultrafiltrate, and the drive fluid pump is configured for connection to the receptacle, such that liquid in the receptacle is supplied as said drive fluid. The liquid in the receptacle may, depending on implementation and/or time point during operation of the ultrafiltration device, contain any one of the above-mentioned priming liquid, ultrafiltrate, and anticoagulant. By using the liquid in the receptacle as drive fluid, it may be possible to reduce the operational complexity and/or enable a more compact design of the ultrafiltration device. It may also serve to reduce the weight and size of the ultrafiltration device since it may obviate the need for storing a separate drive fluid.

In the foregoing embodiment, the drive fluid side of the membrane chamber may be connected to the drive fluid pump on a first fluid path, and the ultrafiltrate side of the blood filter may be configured for connection to the receptacle via a second fluid path that connects to the first fluid path and comprises a one-way valve that opens towards the first fluid path, whereby ultrafiltration may be caused by the drive fluid pump being operated to pump the drive fluid into the receptacle, and wherein at least one of the first and second fluid paths may comprise a flow controller which is operable to control the rate of the ultrafiltration. Such an embodiment enables the use of a single pump, the drive fluid pump, for driving the blood transport in the withdrawal and return phases and for lowering the pressure on the ultrafiltrate side of the blood filter to drive the ultrafiltration through the semipermeable membrane. This may serve to reduce both complexity, cost and energy consumption of the ultrafiltration device, as well as enabling a compact design.

In foregoing embodiment, the ultrafiltrate side of the blood filter may be further connected in fluid communication with the first fluid path on a third fluid path, which may comprise a one-way valve that opens towards the ultrafiltrate side of the blood filter, and flow controllers may be arranged in the first and third fluid paths and be operable to enable transport of the drive fluid into the blood path via the semipermeable membrane. Such an embodiment enables the drive fluid pump to be used also for driving the transport of drive fluid into the blood path. As noted above, the drive fluid may be the liquid in the receptacle and may contain any one of the above-mentioned priming liquid, ultrafiltrate, and anticoagulant. Thus, the transport of drive fluid may serve to prime the blood path at start-up, to provide displacement fluid into the blood path, and to provide anticoagulant into the blood path.

In one embodiment, as an alternative to the combination of drive fluid pump and membrane chamber, the blood pump comprises a reciprocating pump with a reciprocating element that defines a displacement chamber that forms at least part of the buffer vessel. Here, the reciprocating pump operates both as blood pump and buffer vessel. This enables a compact design, and potentially a reduced complexity. In principle any reciprocating pump could be used, including but not limited to piston pumps, plunger pumps, and syringe pumps.

In one embodiment, the ultrafiltrate side of the blood filter is connected to an ultrafiltrate path for fluid communication with a receptacle for receiving the ultrafiltrate, the ultrafiltrate path comprising an ultrafiltrate pump operable to draw ultrafiltrate from the blood side of the blood filter via the semipermeable membrane. In this embodiment, the ultrafiltrate pump is selectively operated to lower the pressure on the ultrafiltrate side of the blood filter to drive the ultrafiltration through the semipermeable membrane. The ultrafiltrate pump may also be reversed to drive the fluid into the blood path via the semipermeable membrane, e.g. for priming, for proving displacement fluid or for providing anticoagulant. Each of the priming liquid, the displacement liquid and the anticoagulant may be pumped through the ultrafiltrate pump from a respective supplemental reservoir. However, a simplified and compact design is enabled by one or more of the priming liquid/displacement liquid/anticoagulant being pumped into the blood path from the receptacle for ultrafiltrate. In one embodiment, the receptacle is pre-loaded with a suitable liquid supply when connected to the ultrafiltrate path. Depending on implementation, the liquid supply may contain one or more of the priming liquid/displacement liquid/anticoagulant.

As an alternative to using an ultrafiltrate pump, the ultrafiltrate side of the blood filter may be connected to an ultrafiltrate path for fluid communication with a receptacle for receiving the ultrafiltrate, the ultrafiltrate path comprising a one-way valve configured to open towards the receptacle. In this embodiment, the ultrafiltration is driven by the blood pump establishing the pressure gradient through the semipermeable membrane. The use of one-way valve may enable a simplified and compact design of the ultrafiltrate device, since the need for a dedicated ultrafiltrate pump is obviated.

A second aspect of the invention is a system for ultrafiltration of blood. The system comprises the ambulatory ultrafiltration device of the first aspect and a disposable container defining a receptacle for receiving the ultrafiltrate. The second aspect shares the advantages and technical effects of the first aspect and its embodiments.

In one specific embodiment of the second aspect, the disposable container contains a supply of at least one of a priming liquid, a displacement liquid and an anticoagulant, which may be supplied to the blood path according to the various embodiments of the first aspect. In one specific embodiment, the supply is contained in the receptacle for ultrafiltrate.

A third aspect of the invention is a method of controlling an ambulatory ultrafiltration device connected to the vascular system of a subject. The ambulatory ultrafiltration device comprising a blood filter having a blood side configured for fluid communication with the vascular system of the subject, an ultrafiltrate side, and a semipermeable membrane disposed between the blood side and the ultrafiltrate side; a buffer vessel in fluid communication with the blood side of the blood filter; and a blood pump. The method comprises the repeated steps of: operating a blood pump to withdraw blood on a blood path from the subject via the blood filter to the buffer vessel, and operating the blood pump to return blood from the reservoir to the subject on the blood path, such that ultrafiltrate is removed from the blood via the semipermeable membrane when the blood is withdrawn from and/or returned to the subject.

The third aspect shares the advantages and technical effects of the first aspect. It is also to be understood that the method of controlling may involve using, obtaining, causing or otherwise providing any of the features defined in the above-mentioned embodiments of the first aspect.

A fourth aspect of the invention is a computer readable medium having a program recorded thereon, the program comprising instructions for causing a computer to perform the method of the third aspect.

A fifth aspect of the invention is a method for ultrafiltration of blood. The method comprises: withdrawing, on a blood path, blood from the vascular system of a subject into a buffer vessel; returning blood from the buffer vessel to the vascular system of the subject on the blood path; and performing ultrafiltration by passing the blood through a blood filter during at least one of the withdrawing and the returning.

The fifth aspect shares the advantages and technical effects of the first aspect. It is also to be understood that the method for ultrafiltration may involve using, obtaining, causing or otherwise providing any of the features defined in the above-mentioned embodiments of the first aspect.

Still other objectives, features, aspects and advantages of the present invention will appear from the following detailed description, from the attached claims as well as from the drawings.

BRIEF DESCRIPTION OF THE DRAWINGS

Embodiments of the invention will now be described herein by way of example only, with reference to the accompanying schematic drawings.

DETAILED DESCRIPTION OF EXEMPLARY EMBODIMENTS

Figure 1:
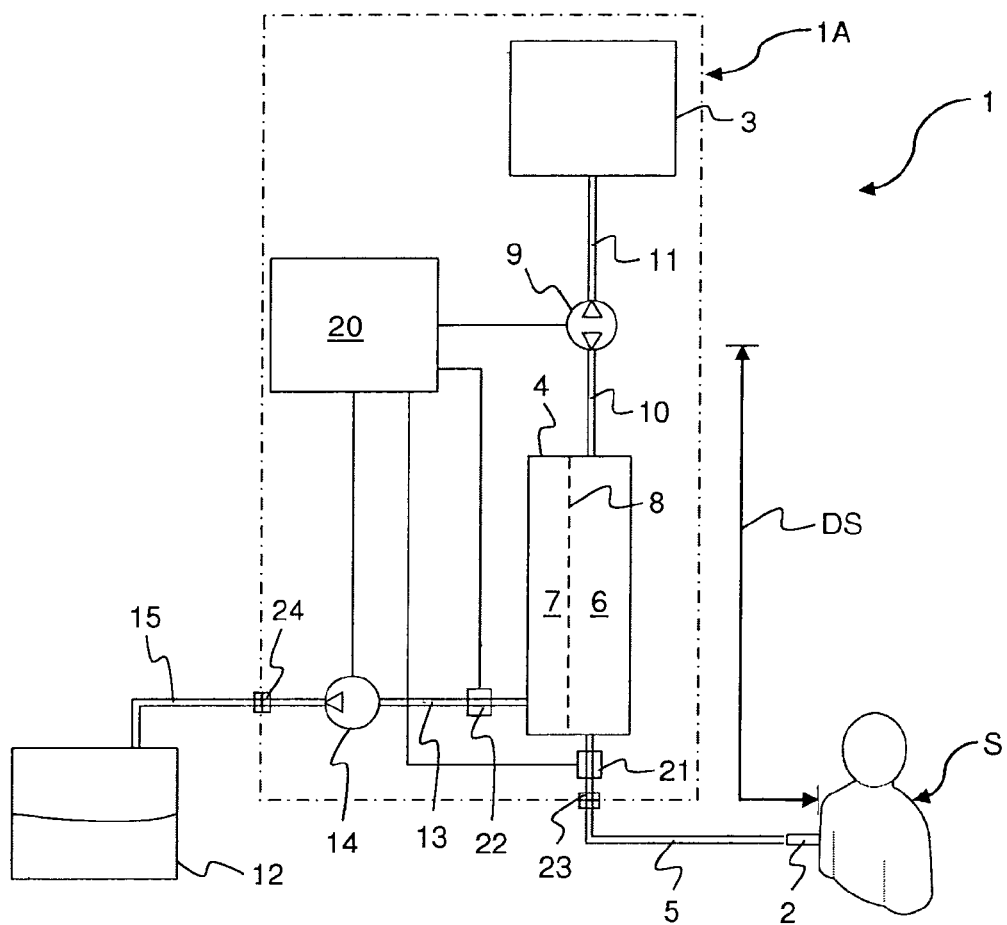
FIG. 1 is a block diagram of an ultrafiltration system according to an embodiment.

Exemplary embodiments of the present invention will now be described with reference to ultrafiltration systems that are designed to be used for ambulatory SCUF or other types of continuous or intermittent ultrafiltration while being worn or otherwise carried by the subject being treated.

Throughout the description, the same reference numerals are used to identify corresponding elements.

FIG. 1 illustrates a system 1 for ultrafiltration according to a first embodiment. The system defines a blood path that extends from an access device 2 for connection to the vascular system of a human or animal subject S to a buffer vessel 3. The access device 2 may be of any suitable type, such as a cannula, a needle, a catheter, etc, and may be adapted for connection to any suitable vascular access, such as fistula, a graft, a Scribner-shunt, a peripheral vein, etc, on any part of the subject's body. The access device 2 is connected to an inlet of a filtration unit 4 via a tubing 5. The filtration unit 4 may be any type of blood filter device (also denoted "hemofiltration device") suitable for ultrafiltration, such as a coil dialyzer, a parallel plate dialyzer, a hollow fiber dialyzer, etc. The filtration unit 4 generally has a blood side 6 and an ultrafiltrate side 7 separated by a semipermeable membrane 8. An outlet on the blood side 6 is connected to a blood pumping device 9 via a tubing 10, and the blood pumping device 9 is connected to the buffer vessel 3 via a tubing 11. The blood pumping device 9 (also denoted "blood pump") may be of any suitable type for pumping blood through a tubing, e.g. a roller or peristaltic pump, a centrifugal pump, etc. As indicated in FIG. 1, the blood pump 9 is operable to pump the blood in both directions in the blood path.

The system 1 also defines an ultrafiltrate path that extends from the ultrafiltrate side 7 of the filtration unit 4 to a filtrate collection vessel 12. An outlet on the ultrafiltrate side 7 is connected via a tubing 13 to a filtrate pumping device 14 (also denoted "filtrate pump"), which is connected to the collection vessel 12 via a tubing 15. The filtrate pump 14 may be of any suitable type, e.g. a roller or peristaltic pump, a centrifugal pump, etc. In the example of FIG. 1, the filtrate pump 14 is operable to pump filtrate from the filtration unit 4 towards the collection vessel 12. The collection vessel 12 may be implemented either as a disposable part which is replaced when filled with ultrafiltrate, or it may be provided with an emptying valve (indicated by 60 in FIGS. 6-7) which can be selectively opened to drain the collection vessel 12. As explained in the Background and Summary sections, the ultrafiltrate is a liquid, mainly water, that is driven through the membrane 8 by a pressure gradient between the blood side 6 and the ultrafiltrate side 7.

The system 1 further includes an electronic control unit 20, which controls the operation of the pumps 9, 14. The control unit 20 may also implement one or more safety functions, by processing signals from one or more safety sensors in the system, exemplified in FIG. 1 by an air detector 21 attached to tubing 5 and a blood leak detector 22 attached to tubing 13. Although not shown in FIG. 1, the system 1 may also include one or more pressure sensors for monitoring the pressure in the blood path and/or in the ultrafiltrate path. The pressure sensor signal(s) may be used by the control unit 20 to control the operation of the pumps 9, 14 and/or to detect system malfunction. Still further, the system 1 includes a power source (not shown), e.g. a battery, for providing electrical power to the control unit 10, the safety sensors 21, 22 and the pumps 9, 14.

Figure 2:
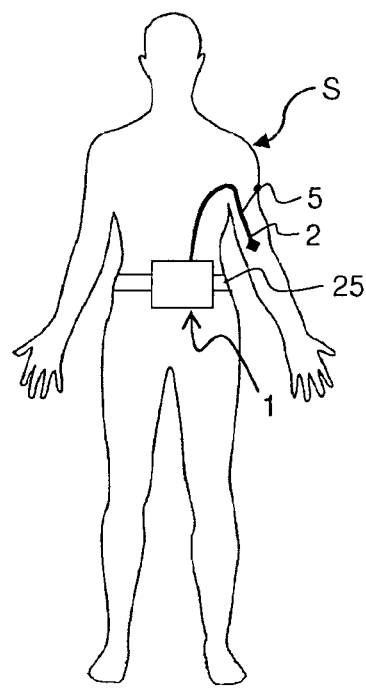
FIG. 2 is a front view of a subject carrying an ambulatory ultrafiltration device according to an embodiment.

FIG. 2 illustrates the system 1 as attached to the subject S and with the access device 2 connected to the vascular access. In the illustrated example, the system 1 is implemented as a unitary device which is strapped around the waist of the subject S access by means of a belt 25. Thereby, the system 1 can be continuously or intermittently operated for ambulatory ultrafiltration of the subject's blood.

Returning to FIG. 1, the system 1 may be provided in the form of a unitary blood processing device 1A, indicated by dashed lines, which contains all functional components for processing the blood (pumps 9, 14, filtration unit 4, control unit 20, power supply, safety sensors 21, 22, etc), as well as a blood input connector 23 and a filtrate output connector 24. The system 1 also includes a separate access device 2 with tubing and a connector for attachment to the blood input connector 23, and a separate filtrate collection vessel with tubing and a connector for attachment to the filtrate output connector 24. The blood processing device 1A may be re-usable, whereas the access device 2 (with tubing and connector) and/or the collection vessel 12 (with tubing and connector) may be disposable parts that are replaced after use.

In an alternative implementation, the system 1 in FIG. 1 is fully integrated into a unitary stand-alone device which is replaced after use, e.g. when the collection vessel 12 is full, or at prescribed intervals.

Figure 3:
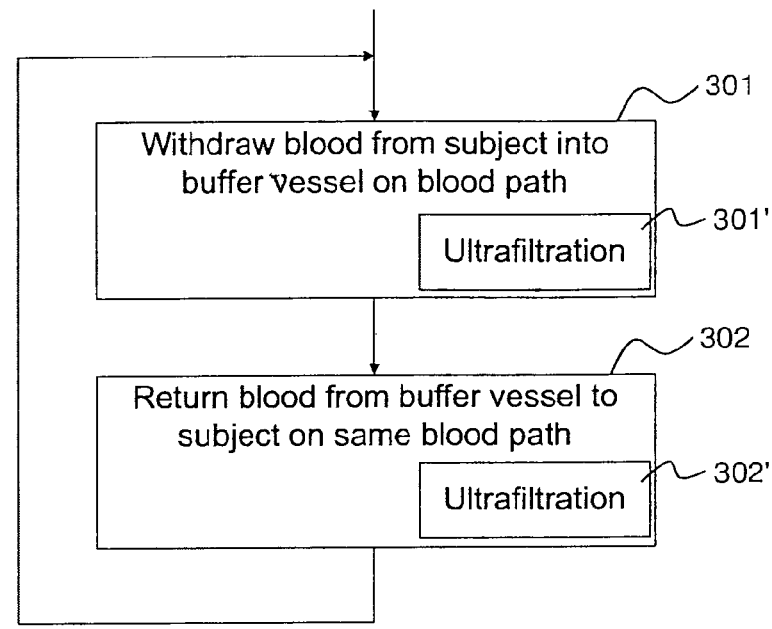
FIG. 3 is a flow chart of a method according to an embodiment.

The operation of the system in FIG. 1 is illustrated in the flow chart of FIG. 3. The treatment is performed in a repetitive two-phase cycle: a withdrawal phase 301 in which the blood pump 9 is operated to draw blood from the subject S through the filtration unit 4 and into the buffer vessel 3, and a return phase 302 in which the blood pump 9 is operated to push blood from the buffer vessel 3 through the filtration unit 4 back into the subject S. As indicated in FIG. 3, the filtrate pump 14 may be operated in either the withdrawal phase (step 301') or the return phase (step 302'), or both, to generate the pressure gradient that drives the ultrafiltrate through the membrane 8 and into the collection vessel 12.

Figure 4:
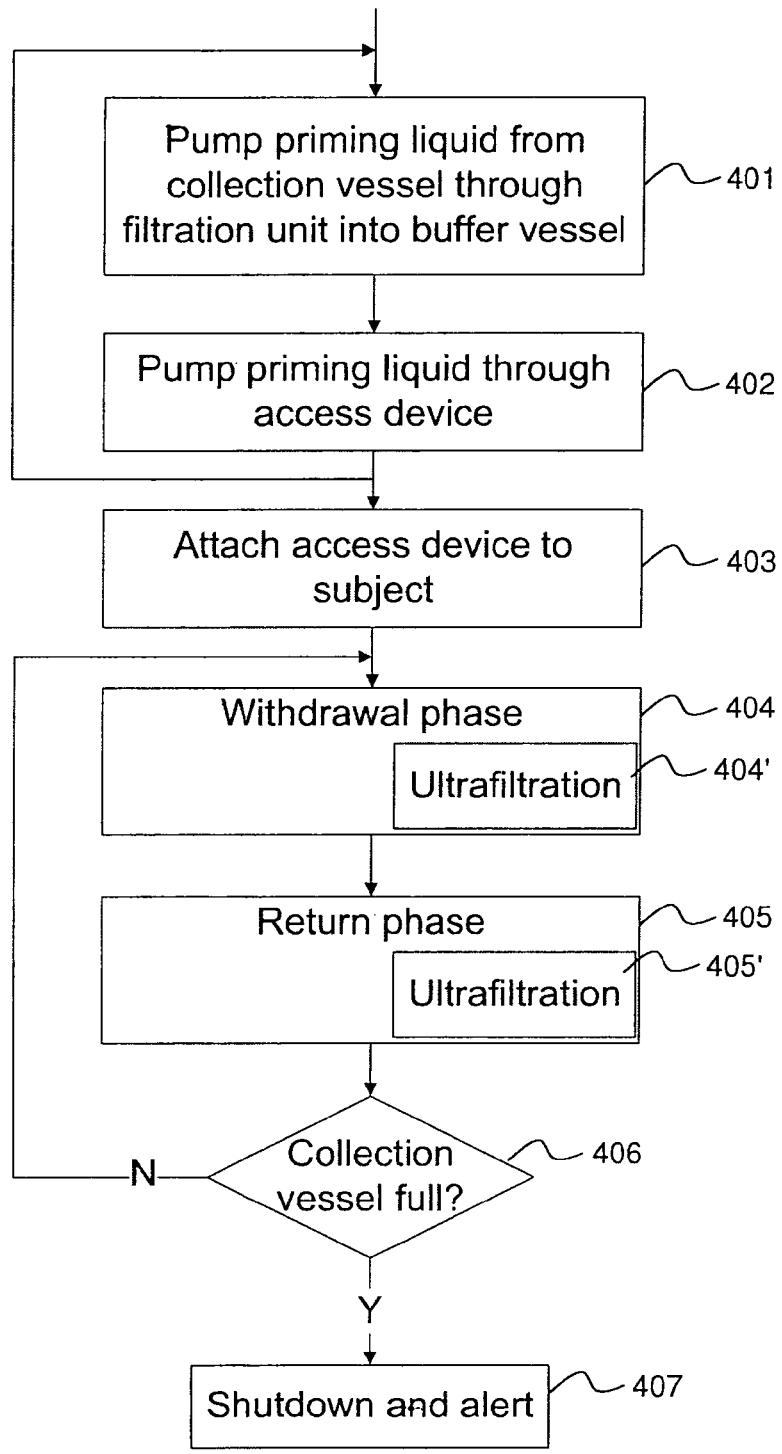
FIG. 4 is a flow chart of a control method according to an embodiment.

FIG. 4 is a flow chart that illustrates a variant of the general method in FIG. 3. The method in FIG. 4 presumes that the collection vessel 12 initially contains a supply of a sterile priming liquid, and that the filtrate pump 14 is reversible, i.e. able to also pump a liquid from the collection vessel 12 into the filtration unit 4. With reference to FIG. 1, it is realized that the collection vessel 12 should be arranged with tubing 15 connected at the bottom of the vessel 12, so that the liquid can be pumped out of the vessel 12.

The method is illustrated at start-up of the system, i.e. before connecting the access device 2 to the subject S. In step 401, the filtrate pump 14 is operated to pump priming liquid from the collection vessel 12 into the filtration unit 4, whereby a reversed pressure gradient is established through the membrane 8 to drive the priming liquid into the blood side 6 of the filtration unit 4. Concurrently, the blood pump 9 is operated to draw the priming liquid into the buffer vessel 3. In step 402, the blood pump 9 is reversed to drive the priming liquid and any air from the buffer vessel 3, through the tubings 11, 10, the filtration unit 4 and the tubing 5 and out of the access device 2. The filtrate pump 14 may or may not be stopped in this step. Steps 401 and 402 are then repeated a number of times (e.g. 1-5). In step 403, the access device 2 is connected to the subject S. The system 1 is then repeatedly operated in the withdrawal phase 404 and the return phase 405, while ultrafiltrate being extracted 404', 405' from the blood in one or both of these phases. In the example of FIG. 4, the operation continues until the collection vessel 12 is full (step 406). Then, in step 407, the pumps 9, 14 are stopped and an alert is generated to inform the subject S that it is time to empty or replace the collection vessel 12, or to replace the entire system 1. The decision in step 406 may be based on an output signal from a level sensor (not shown) in the vessel 12, or a signal from a pressure sensor (not shown) in the vessel 12 or in the ultrafiltrate path, or a signal from a scale (not shown) for indicating the weight of the vessel 12, or any other sensor that enables assessment of the level of liquid in the vessel 12. Alternatively, the amount of ultrafiltrate may be estimated by volumetric calculations, e.g. based on the number of withdrawal/return phases or based on a signal from flow meters (not shown) in the ultrafiltrate path or in the blood path.

The skilled person realizes that the system 1 should be designed according to:

$$V_{BV} > V_{BP} + V_{UF}$$

where $V_{BV}$ is the volume of blood that is drawn into the buffer vessel 3 during each withdrawal phase, $V_{BP}$ is the volume of the blood path between the buffer vessel 3 and the subject S, and $V_{UF}$ is the volume of ultrafiltrate extracted from the blood during each treatment cycle (i.e. a withdrawal phase and a return phase).

However, it has been found that such a condition may not be sufficient to prevent that a fraction of the blood in a certain part of the blood path is not subjected to ultrafiltration and returned to the subject S. This part of the blood path, denoted dead space and indicated by DS in FIG. 1, extends from the pump 9 to the access device 2. To reduce the influence of the dead space DS, it is proposed to intermittently (e.g. every 5-10 cycles) reverse the filtrate pump 14 to drive liquid (ultrafiltrate) from the vessel 12 via the filtration unit 4 into the blood path, during at least part of a return phase, or after the return phase but before the withdrawal phase. This "backfiltration" drives ultrafiltrate into the blood path, where the ultrafiltrate acts to displace at least some of the blood in the dead space DS into the subject S. This displacement will decrease the fraction of blood that may be trapped in the dead space DS.

In the following, different variants and extensions of the system in FIG. 1 will be discussed in relation to FIGS. 5-12. For the sake of brevity, the following discussion will focus on differences in structure and operation with respect to the system in FIG. 1. Thus, unless explicitly stated otherwise, it is to be assumed that the foregoing description is equally applicable to the systems in FIGS. 5-12.

Figure 5:
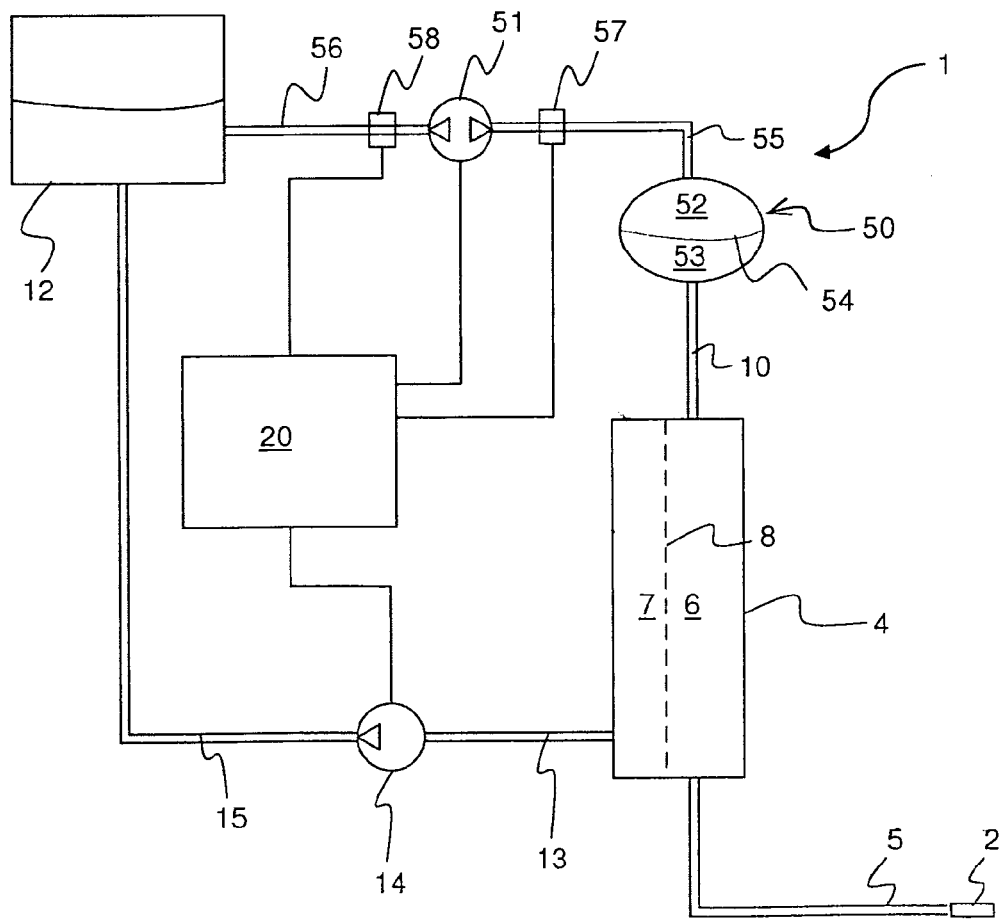
FIG. 5 is a block diagram of an ultrafiltration system according to an embodiment.
Figure 6:
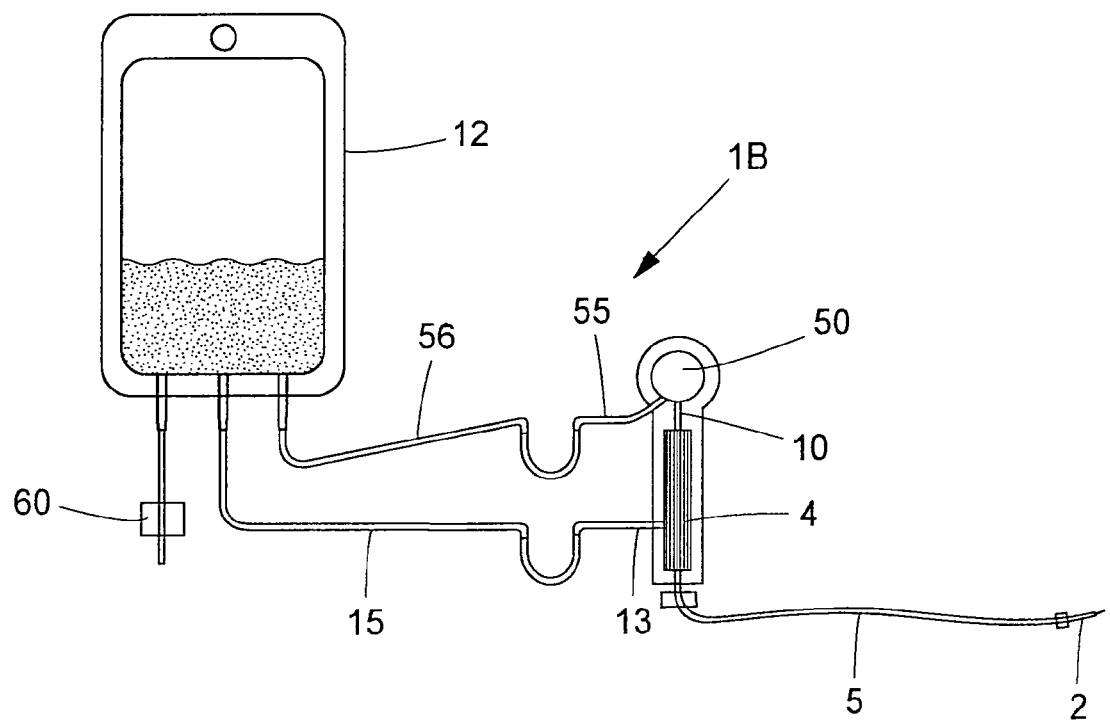
FIG. 6 is front view of an ultrafiltration system according to an embodiment

In the system of FIG. 5, the blood pump and the buffer vessel are implemented by a membrane pump formed by diaphragm chamber 50 and a further filtrate pump 51. The diaphragm chamber 50 is divided into a drive fluid side 52 and a blood side 53, separated by a flexible impermeable diaphragm 54. The pump 51 is arranged generate the return phase by pumping, via tubing 55, ultrafiltrate from the vessel 12 to the drive fluid side 52, whereby the diaphragm 54 is caused to flex such that blood on the blood side 53 is pumped into the blood path. By reversing the pump 51, ultrafiltrate is pumped back into the vessel 12 from the drive fluid side 52, causing the diaphragm 54 to flex and draw blood into the blood side 53 from the blood path. To ensure that the drive fluid pump 51 and the diaphragm chamber 50 are operating properly, the control unit 20 may be arranged to monitor the pressure in the drive fluid path, e.g. via pressure sensors 57, 58 arranged on both sides of the drive fluid pump 51. One advantage of the embodiment in FIG. 5 is that a simpler pumping device can be used for pumping drive fluid (ultrafiltrate) compared to blood (cf. FIG. 1). Another advantage is that the diaphragm chamber 50 and the filtration unit 4 can be integrated with a small separation between the buffer vessel (i.e. the blood side 53) and the filtration unit 4, e.g. as shown in FIG. 6. The small separation may, e.g., be advantageous to reduce the above-mentioned dead space and to provide a compact and rugged device suited for ambulatory blood treatment. FIG. 6 further illustrates an embodiment in which all fluid containing parts (drive fluid path, ultrafiltrate path, blood path and vessel 12) are integrated into a coherent component 1B.

Figure 7:
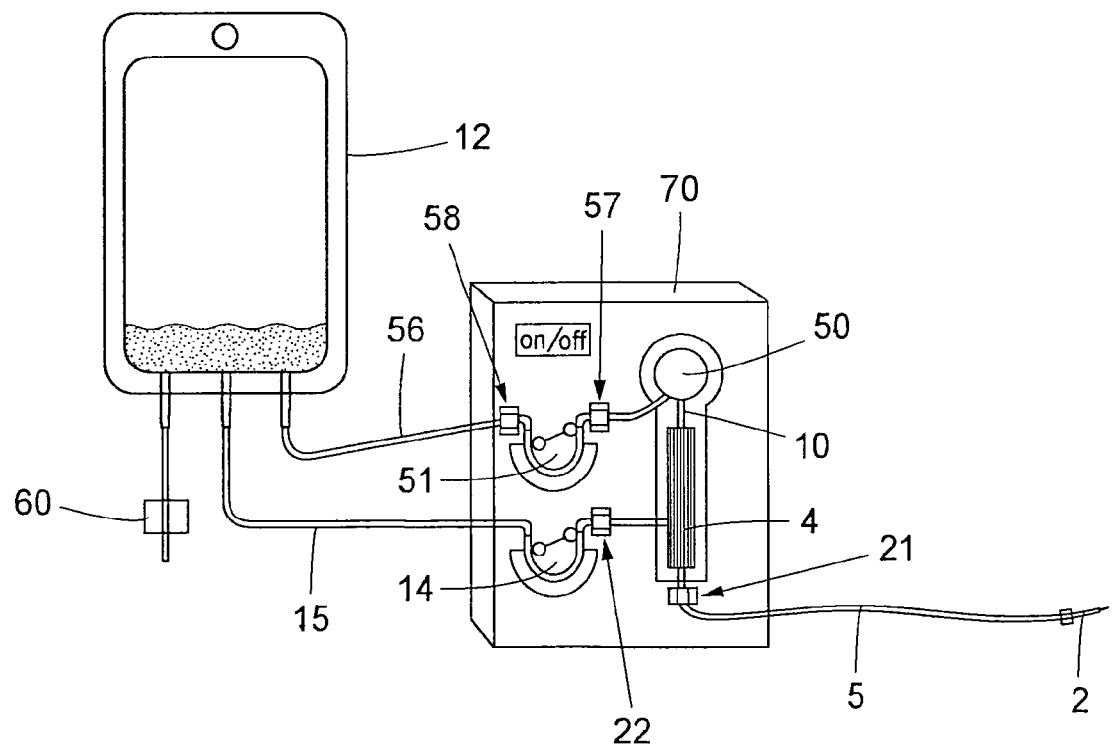
FIG. 7 is a view, partially in perspective, of an ultrafiltration system according to an embodiment

FIG. 7 illustrates a further example of an integration of the coherent component 1B in FIG. 6 with a chassis 70. The chassis 70 contains the pumps 14, 51, the pressure sensors 57, 58, an air detector 21 and a blood leak detector 22, together with the control unit, the power supply (not shown) and an operator's interface (exemplified by an on/off switch). An operable ultrafiltration device 1 is formed mounting the component 1B onto the front face of the chassis 70. In this embodiment, the component 1B may be removed from the chassis 70 and disposed when the bag 12 is full, or alternatively the bag 12 may be drained (via the emptying valve 60) and the component 1B be re-used.

Figure 8:
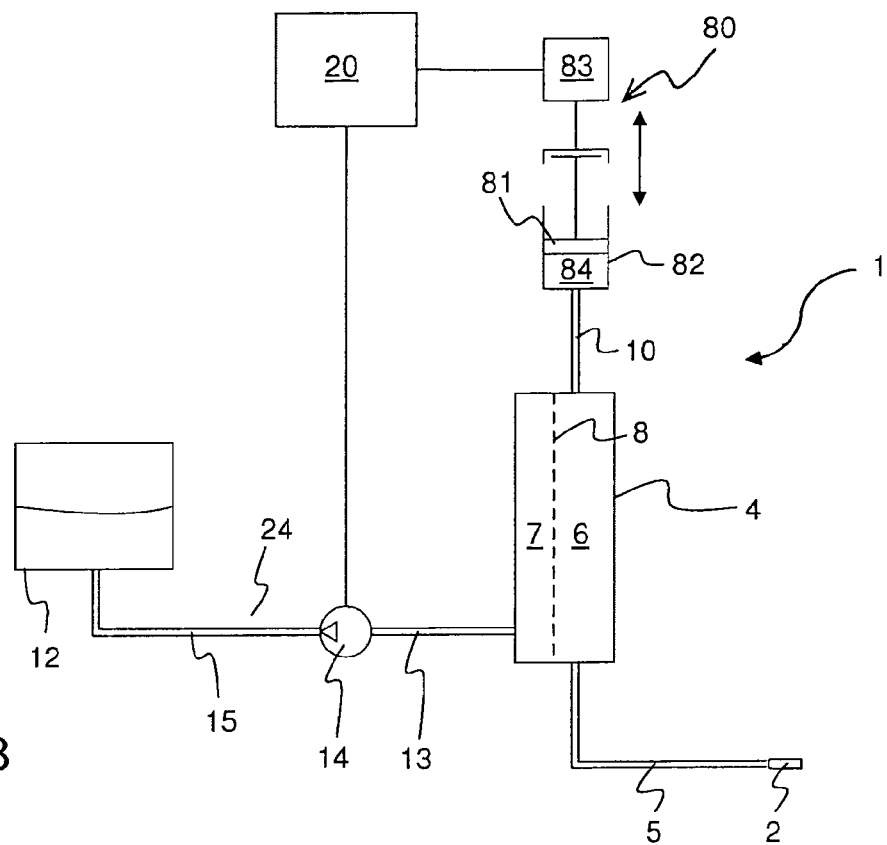
FIGS. 8-12 are block diagrams of ultrafiltration systems according to various embodiments.

FIG. 8 illustrates a variant of the embodiment in FIG. 1, where the blood pump and the buffer vessel are implemented by a reciprocating pump 80. The pump 80 includes a pusher 81 which is driven to reciprocate back and forth in a cylinder 82 by means of an electric motor 83, e.g. a stepper motor or a DC motor, subject to control by the control unit 20. The buffer vessel is formed by the cylinder chamber 84 which is defined between the cylinder 82 and the reciprocating element 81. In one embodiment, the reciprocating pump 80 is a syringe pump in which the pusher 81 and the cylinder 82 are part of a syringe, which may or may not be replaceable.

Figure 9:
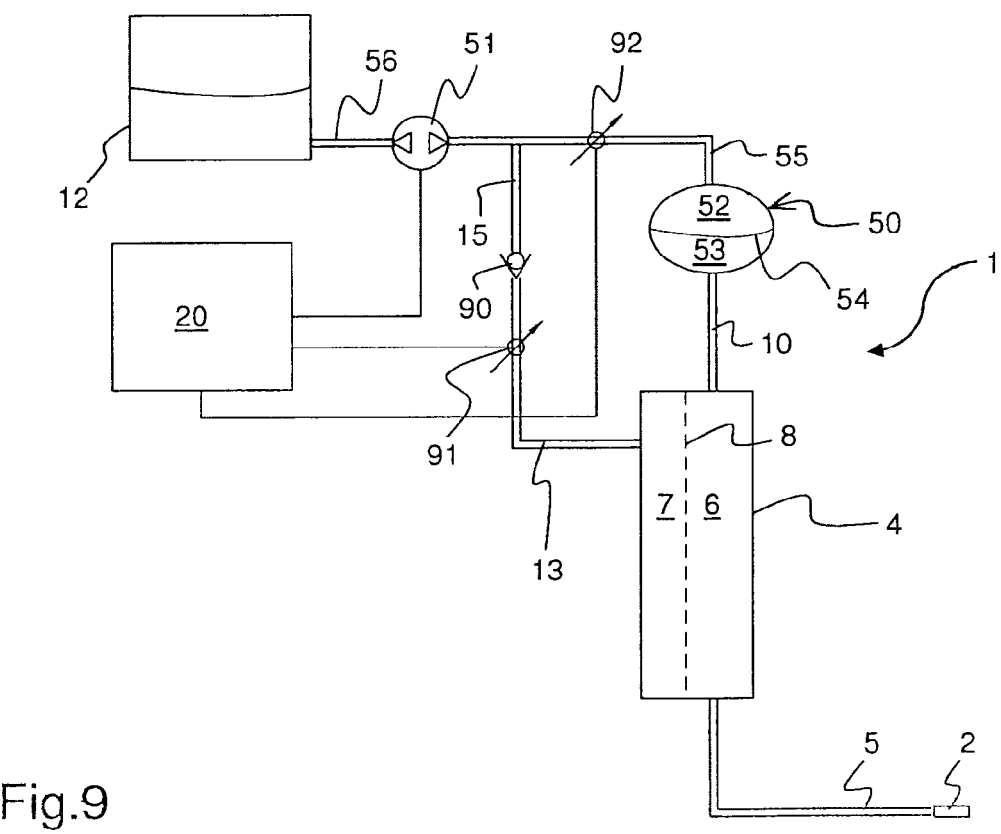

FIG. 9 illustrates a variant of the embodiment in FIG. 5, where one of the filtrate pumps is replaced by a passive device 90, such as a check valve, that allows ultrafiltrate to pass from the filtration unit 4 to the vessel 12, but not in the opposite direction. The filtrate outlet of the filtration unit 4 is connected, via the check valve 90, to the tubing 55 intermediate the filtrate pump 51 and the diaphragm chamber 50. Flow controllers 91, 92, e.g. flow control valves, are arranged in the filtrate flow paths from the filtrate unit 4 and the diaphragm chamber 50, respectively. The flow controllers 91, 92 are operated by the control unit 20 to set the ratio between the flow of ultrafiltrate from the drive fluid chamber 52 and the flow of ultrafiltrate from the filtration unit 4, when the filtrate pump 51 is operated to draw ultrafiltrate into the vessel 12. It is realized that the ultrafiltration, in this example, is generated during the withdrawal phase, and that the ultrafiltration rate is controlled by the respective settings of the flow controllers 91, 92. In a variant, only one flow controller is provided in one of the filtrate flow paths. The flow controller(s) may be set in dependence of the signals from one or more pressure sensors (cf. 57, 58 in FIG. 5).

Returning to the embodiment in FIG. 1, it should be realized that the filtrate pump 14 may be replaced by a check valve or a similar passive device that opens towards collection vessel 12, but closes in the opposite direction. In such an embodiment, ultrafiltration through the membrane 8 is driven by the pressure on the blood side 6 of the filtration unit 4, which e.g. may be inherently created during the return phase by the flow restriction provided by the access device 2, or may be created by selectively restricting the flow in the blood path (e.g. by means of a flow controller) during the withdrawal and/or return phases.

Figure 10:
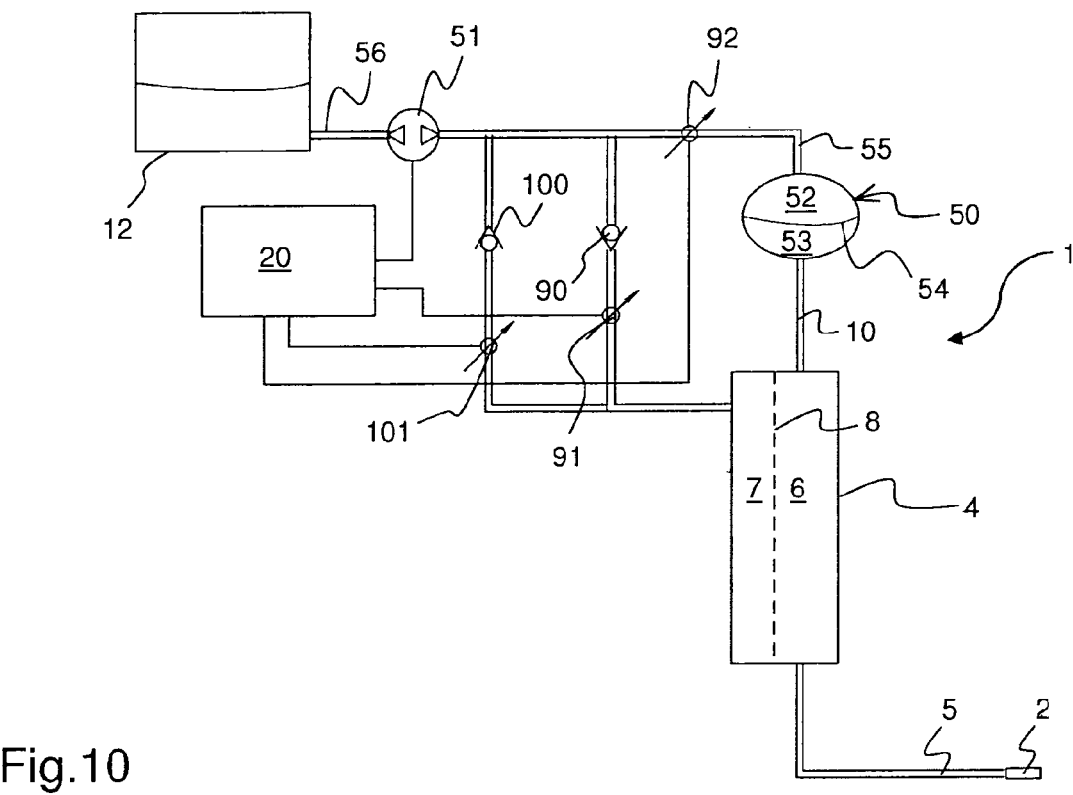

FIG. 10 illustrates a variant of the embodiment in FIG. 9, in which a further filtrate path is provided between the filtrate outlet of the filtration unit 7 and the tubing 55 intermediate the filtrate pump 51 and the diaphragm chamber 50, and is provided with a flow controller 101 and a check valve 100 that opens towards the filtration unit 4 but closes in the opposite direction. This embodiment enables priming of the blood path and/or displacement of blood in the dead space via backfiltration.

Figure 11:
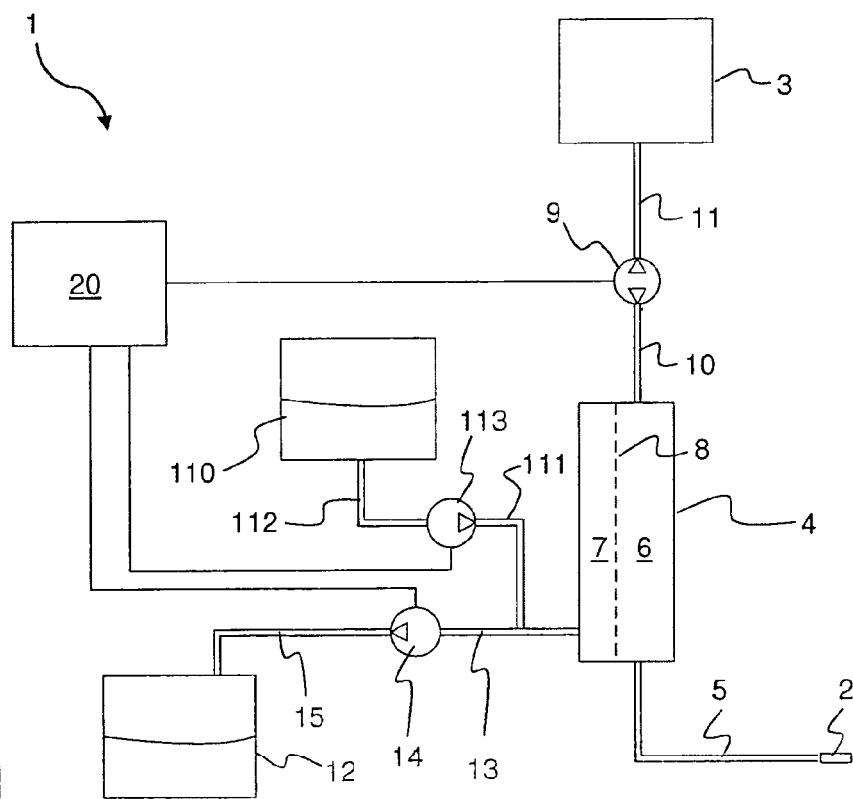

FIG. 11 illustrates a variant of the embodiment in FIG. 1 (or any of the other embodiments disclosed herein), which includes a separate vessel 110 that holds the sterile priming liquid. In the illustrated embodiment, the priming vessel 110 is connected via tubings 111, 112 and a dedicated priming pump 113 to the ultrafiltrate path between the filtrate pump 14 and the filtrate outlet on the filtration unit 4. The filtrate pump 14 is operated when the priming pump 113 is stopped and vice versa, such that ultrafiltrate is drawn into the collection vessel 12 and priming liquid is pumped into the blood path, respectively. It is to be understood that the pumps 14, 113 are occluding when they are stopped. In a variant (not shown), the priming pump 113 is instead connected to a second (dedicated) port on the ultrafiltrate side 7 of the filtration unit 4. In either variant, the collection vessel 12 and the priming vessel 110 may be implemented by different compartments in a single container/bag, or by separate containers/bags.

Figure 12:
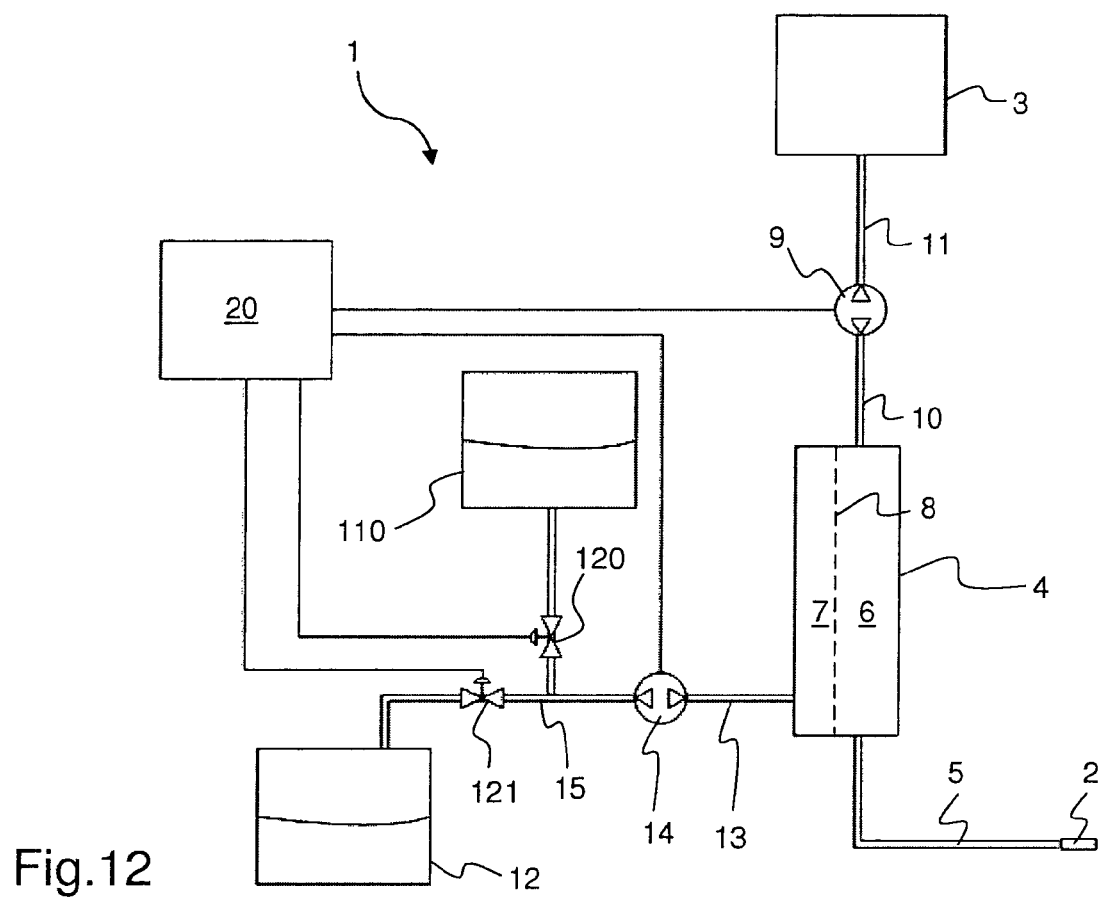

FIG. 12 illustrates a variant of the embodiment in FIG. 11, where a single reversible filtrate pump 14 is arranged in the ultrafiltrate path between the collection vessel 12 and the filtration unit 4. The priming vessel 110 is connected to the ultrafiltrate path between the collection vessel 12 and the filtrate pump 14, with on/off valves 120, 121 being arranged in the priming and ultrafiltrate paths. The valves 120, 121 are selectively switched, by the control unit 20, such that ultrafiltrate is drawn into the collection vessel 12 and priming liquid is backfiltrered into the blood path, respectively.

In the embodiments shown in FIGS. 11-12, the priming vessel 110 may contain a combination of a sterile priming liquid and an anticoagulant, such as heparin or citrate. Thereby, the liquid in the priming vessel 110 may not only be used for priming the blood path at start-up, but also to intermittently add anticoagulant to the blood in the blood path, by backfiltration through the membrane 7 in the filtration unit 4.

According to an alternative (which may be implemented in any of the embodiments shown herein), the system 1 is provided with a separate anticoagulant vessel (not shown) which is connected to the filtration unit 4 in the same way as the priming vessel 110 in FIG. 11 or FIG. 12. The anticoagulant vessel may be implemented by a dedicated compartment in a container/bag that also includes the collection vessel 12 and/or priming vessel 110, or by a separate container/bag.

According to yet another alternative (which may be implemented in any of the embodiments shown herein), the anticoagulant is contained in the collection vessel 12. Thereby, the anticoagulant can be intermittently driven into the blood path via backfiltration. It is realized that the anticoagulant in the collection vessel 12 will be gradually diluted by the ultrafiltrate that is extracted from the blood. The control unit 20 may at least partly compensate for this by gradually increasing of the duration of the backfiltration events and/or the frequency of backfiltration events.

In the above-described embodiments and variants, all or part of the functionality of the control unit 20 may be provided by dedicated hardware and/or by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The computing device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The computing device may include one or more communication interfaces, such as a serial interface, a parallel interface, a USB interface, a wireless interface, a network adapter, etc, as well as one or more data acquisition devices, such as an A/D converter. The special-purpose software may be provided to the computing device on any suitable computer-readable medium, including a record medium, a read-only memory, or an electrical carrier signal.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

For example, although the blood pump is arranged after the filtration unit (as seen from the subject) in all illustrated embodiments, the blood pump may instead be arranged between the filtration unit and the access device.

Generally speaking, the skilled person readily understands that different measures may need to be taken to achieve ultrafiltration in the withdrawal phase and the return phase, respectively, and likewise to prevent backfiltration at other times (unless when backfiltration is indeed desired), and that these measures may differ depending on the placement of the blood pump, the design of the filtrate unit, the type and arrangement of tubings, etc.

The invention claimed is:

1. An ambulatory ultrafiltration device for connection to the vascular system of a subject, comprising:
   a blood filter having a blood side configured for fluid communication with the vascular system of the subject, an ultrafiltrate side configured for fluid communication with a receptacle for receiving ultrafiltrate, and a semipermeable membrane disposed between the blood side and the ultrafiltrate side;
   a blood pump including a membrane chamber which defines a blood side and a drive fluid side separated by a flexible membrane, the blood side of the membrane chamber connected in fluid communication with the blood side of the blood filter, the blood pump operable to alternate between a withdrawal phase and a return phase, wherein the withdrawal phase comprises blood being withdrawn along a blood path in fluid communication with the subject and the blood filter to the blood side of the membrane chamber, and the return phase comprises blood being returned from the blood side of the membrane chamber to the subject on said blood path;
   a drive fluid pump in fluid communication with the drive fluid side of the membrane chamber and the receptacle, the drive fluid pump operable to pump liquid from the receptacle out of and into the drive fluid side of the membrane chamber during the withdrawal and return phases; and a control unit programmed to cause the blood filter to perform ultrafiltration, such that the blood filter separates ultrafiltrate from plasma in the blood without changing a plasma concentration of small solutes in the blood, during at least one of the withdrawal and return phases.

2. The ambulatory ultrafiltration device of claim 1, further comprising a source of anticoagulant to be supplied to the blood path.

3. The ambulatory ultrafiltration device of claim 2, wherein said source of anticoagulant supplies the anticoagulant through the semipermeable membrane.

4. The ambulatory ultrafiltration device of claim 1, further comprising means for intermittently supplying a displacement liquid to the blood path during the return phase or intermediate the return phase and the withdrawal phase.

5. The ambulatory ultrafiltration device of claim 4, wherein said means for intermittently supplying a displacement liquid is operable to supply the displacement liquid through the semipermeable membrane.

6. The ambulatory ultrafiltration device of claim 4, wherein said displacement liquid comprises an anticoagulant.

7. The ambulatory ultrafiltration device of claim 4, wherein said displacement liquid comprises said ultrafiltrate.

8. The ambulatory ultrafiltration device of claim 1, further comprising a source of priming liquid configured to supply priming liquid to the blood path.

9. The ambulatory ultrafiltration device of claim 8, wherein said source of priming liquid supplies the priming liquid to the blood path through the semipermeable membrane.

10. The ambulatory ultrafiltration device of claim 1, wherein the drive fluid side of the membrane chamber is connected to the drive fluid pump on a first fluid path, wherein the ultrafiltrate side of the blood filter is configured for connection to the receptacle via a second fluid path that connects to the first fluid path and comprises a one-way valve that opens towards the first fluid path, whereby ultrafiltration is caused by the drive fluid pump being operated to pump the ultrafiltrate into the receptacle, and wherein at least one of the first and second fluid paths comprises a flow controller which is operable to control the rate of the ultrafiltration.

11. The ambulatory ultrafiltration device of claim 10, wherein the ultrafiltrate side of the blood filter is further connected in fluid communication with the first fluid path on a third fluid path, which comprises a one-way valve that opens towards the ultrafiltrate side of the blood filter, wherein flow controllers are arranged in the first and third fluid paths and operable to enable transport of the drive fluid into the blood path through the semipermeable membrane.

12. The ambulatory ultrafiltration device of claim 1, wherein the ultrafiltrate side of the blood filter is connected to an ultrafiltrate path for fluid communication with the receptacle for receiving the ultrafiltrate, the ultrafiltrate path comprising a one-way valve configured to open towards the receptacle.

13. The ambulatory ultrafiltration device of claim 1, wherein the ultrafiltrate side of the blood filter is connected to an ultrafiltrate path for fluid communication with the receptacle for receiving the ultrafiltrate, the ultrafiltrate path comprising an ultrafiltrate pump operable to draw ultrafiltrate from the blood side of the blood filter through the semipermeable membrane.

14. The ambulatory ultrafiltration device of claim 13, wherein the ultrafiltrate pump is further operable to pump at least one of a priming liquid, a displacement liquid and an anticoagulant into the blood path through the semipermeable membrane.

15. The ambulatory ultrafiltration device of claim 14, wherein said at least one of a priming liquid, a displacement liquid and an anticoagulant is pumped from the receptacle.

16. The ambulatory ultrafiltration device of claim 14, wherein the receptacle is pre-loaded with a supply of said at least one of a priming liquid, a displacement liquid and an anticoagulant when connected to the ultrafiltrate path.

17. The ambulatory ultrafiltration device of claim 14, wherein the ultrafiltrate path is arranged for selective communication with a supplemental reservoir containing said at least one of a priming liquid, a displacement liquid and an anticoagulant.

18. The ambulatory ultrafiltration device of claim 1, wherein the blood side of the blood filter is in fluid communication with an access device for connection to the vascular system of the subject.

19. A system for ultrafiltration of blood, comprising the ambulatory ultrafiltration device of claim 1 and a disposable container defining a receptacle for receiving the ultrafiltrate.

20. The system of claim 19, wherein the disposable container contains a supply of at least one of a priming liquid, a displacement liquid and an anticoagulant.

21. The system of claim 19, wherein said supply is contained in the receptacle.

22. The ambulatory ultrafiltration device of claim 1, further comprising: a chassis configured to be worn by and move with the subject, and an assembly detachably mounted to the chassis, the assembly comprising at least the blood filter.

23. The ambulatory ultrafiltration device of claim 22, wherein the assembly is a disposable component.

24. The ambulatory ultrafiltration device of claim 22, wherein the assembly further comprises the membrane chamber.

25. The ambulatory ultrafiltration device of claim 22, wherein the drive fluid pump is integrated in said chassis and configured for engagement with a drive fluid tubing segment included in the assembly.

26. The ambulatory ultrafiltration device of claim 25, wherein the chassis comprises an ultrafiltrate pump operable to remove from the ultrafiltrate side of the blood filter ultrafiltrate passing through the semipermeable membrane from the blood in the blood side, the ultrafiltrate pump being configured for engagement with an ultrafiltrate tubing segment included in the assembly.

27. The ambulatory ultrafiltration device of claim 25, wherein the receptacle is connected to the drive fluid side of the membrane chamber by the drive fluid tubing segment.

28. An ambulatory ultrafiltration device for connection to the vascular system of a subject, comprising:
 a blood filter having a blood side configured for fluid communication with the vascular system of the subject, an ultrafiltrate side, and a semipermeable membrane disposed between the blood side and the ultrafiltrate side;
 a membrane chamber having a blood side and a drive fluid side separated by a flexible membrane, wherein the blood side of the membrane chamber is in fluid communication with the blood side of the blood filter; and
 a drive fluid pump in fluid communication with the drive fluid side of the membrane chamber, wherein the drive fluid pump is operable to pump a liquid drive fluid out of and into the drive fluid side of the membrane chamber to cause the blood side of the membrane chamber to alternate between a withdrawal phase and a return phase, wherein the withdrawal phase comprises blood being withdrawn along a blood path in fluid communication with the subject and the blood filter to the blood side of the membrane chamber, and the return phase comprises blood being returned from the blood side of the membrane chamber to the subject along said blood path;

a control unit programmed to control the drive fluid pump to perform ultrafiltration, such that the blood filter separates ultrafiltrate from the blood during at least one of the withdrawal and return phases.

29. An ambulatory ultrafiltration device for connection to the vascular system of a subject, comprising:
- a blood filter having a blood side configured for fluid communication with the vascular system of the subject, an ultrafiltrate side configured for fluid communication with a receptacle for receiving ultrafiltrate, and a semipermeable membrane disposed between the blood side and the ultrafiltrate side;
- a blood pump including a membrane chamber which defines a blood side and a drive fluid side separated by a flexible membrane, the blood side of the membrane chamber connected in fluid communication with the blood side of the blood filter, the blood pump operable to alternate between a withdrawal phase and a return phase, wherein the withdrawal phase comprises blood being withdrawn along a blood path in fluid communication with the subject and the blood filter to the blood side of the membrane chamber, and the return phase comprises blood being returned from the blood side of the membrane chamber to the subject along said blood path;
- a drive fluid pump in fluid communication with the drive fluid side of the membrane chamber and the receptacle, the drive fluid pump operable to pump liquid from the receptacle out of and into the drive fluid side of the membrane chamber during the withdrawal and return phases; and
- a control unit programmed to cause the blood filter to separate ultrafiltrate from the blood during at least one of the withdrawal and return phases.

* * * * *